US010502799B2

(12) United States Patent
Goodman et al.

(10) Patent No.: US 10,502,799 B2
(45) Date of Patent: Dec. 10, 2019

(54) FIBER OPTIC NUCLEAR MAGNETIC RESONANCE SENSOR

(71) Applicant: Halliburton Energy Services, Inc., Houston, TX (US)

(72) Inventors: George David Goodman, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 24 days.

(21) Appl. No.: 15/549,052

(22) PCT Filed: Mar. 31, 2015

(86) PCT No.: PCT/US2015/023600
§ 371 (c)(1),
(2) Date: Aug. 4, 2017

(87) PCT Pub. No.: WO2016/159979
PCT Pub. Date: Oct. 6, 2016

(65) Prior Publication Data
US 2018/0038926 A1    Feb. 8, 2018

(51) Int. Cl.
*G01R 33/36* (2006.01)
*G01R 33/32* (2006.01)
(Continued)

(52) U.S. Cl.
CPC ....... *G01R 33/3692* (2013.01); *G01R 33/323* (2013.01); *G01V 3/32* (2013.01); *G01N 24/081* (2013.01); *G01R 33/383* (2013.01)

(58) Field of Classification Search
CPC .................. G01R 33/323; G01R 33/3692; G01R 33/383; G01R 33/032; G01R 33/0322;
(Continued)

(56) References Cited

U.S. PATENT DOCUMENTS 4,814,706 A    3/1989 Rempt
4,904,940 A    2/1990 Rempt
(Continued)

FOREIGN PATENT DOCUMENTS

WO    WO 2013/103908 A1    7/2013

OTHER PUBLICATIONS

International Search Report and the Written Opinion of the International Search Authority, or the Declaration, dated Nov. 13, 2015, PCT/US2015/023600, 18 pages, ISA/KR.
(Continued)

*Primary Examiner* — Steven L Yeninas
(74) *Attorney, Agent, or Firm* — Haynes and Boone, LLP (57) ABSTRACT

Various embodiments include a fiber optic nuclear magnetic resonance (NMR) sensor tool device and systems. One such tool includes a permanent magnet that generates a static magnetic field. A transmit antenna in the tool can operate to transmit a time-varying signal that is orthogonal to the static magnetic field. A fiber optic sensor element includes a coating that phase modulates a light signal traveling in the fiber when the coating is exposed to a varying field (e.g., a received, reflected magnetic field corresponding to the transmitted time-varying signal). The coating may be one of a magnetostrictive coating or a piezoelectric coating. Additional apparatus, systems, and methods are disclosed.

22 Claims, 5 Drawing Sheets

(51) Int. Cl.
*G01V 3/32* (2006.01)
*G01R 33/383* (2006.01)
*G01N 24/08* (2006.01)

(58) Field of Classification Search
CPC .. G01R 33/0325; G01R 33/0327; G01V 3/32; E21B 47/122; E21B 47/123; G01N 24/08; G01N 24/081
USPC ............................................. 324/303, 244.1
See application file for complete search history.

(56) References Cited

U.S. PATENT DOCUMENTS

| | | | |
|---|---|---|---|
| 5,095,514 | A | 3/1992 | Curtis |
| 5,831,433 | A * | 11/1998 | Sezginer ................ G01V 3/32 324/303 |
| 5,898,517 | A * | 4/1999 | Weis .................... E21B 47/123 356/32 |
| 6,215,304 | B1 * | 4/2001 | Slade ................... G01N 24/081 324/303 |
| 6,326,785 | B1 | 12/2001 | Kruspe |
| 6,728,165 | B1 | 4/2004 | Roscigno et al. |
| 7,140,435 | B2 | 11/2006 | Defretin et al. |
| 7,345,485 | B2 | 3/2008 | Jevtic et al. |
| 7,900,699 | B2 | 3/2011 | Ramos et al. |
| 8,035,393 | B2 | 10/2011 | Tenghamn et al. |
| 8,074,713 | B2 | 12/2011 | Ramos et al. |
| 8,354,939 | B2 | 1/2013 | McDaniel et al. |
| 8,604,791 | B2 | 12/2013 | Vaughan, Jr. et al. |
| 8,605,542 | B2 | 12/2013 | Coates et al. |
| 2003/0169956 | A1 | 9/2003 | Lange et al. |
| 2004/0116801 | A1 | 6/2004 | Konings et al. |
| 2006/0151179 | A1 | 7/2006 | Boyadjieff et al. |
| 2007/0126594 | A1 * | 6/2007 | Atkinson .............. E21B 47/123 340/853.1 |
| 2010/0001730 | A1 | 1/2010 | Stephenson et al. |
| 2010/0201359 | A1 | 8/2010 | Rottengatter |
| 2010/0309750 | A1 | 12/2010 | Brady |
| 2010/0315081 | A1 | 12/2010 | Chanpura et al. |
| 2011/0139447 | A1 | 6/2011 | Ramos et al. |
| 2011/0156705 | A1 | 6/2011 | Chan et al. |
| 2012/0062230 | A1 | 3/2012 | Vaughan, Jr. et al. |
| 2012/0235677 | A1 | 9/2012 | Blanz et al. |
| 2013/0056197 | A1 | 3/2013 | Maida et al. |
| 2013/0342210 | A1 * | 12/2013 | Stokely ................. G01R 33/26 324/346 |
| 2014/0064028 | A1 | 3/2014 | Coates et al. |
| 2014/0097846 | A1 | 4/2014 | Lemaire et al. |
| 2014/0111348 | A1 | 4/2014 | Skinner et al. |
| 2014/0159715 | A1 | 6/2014 | McEwen-King |
| 2014/0174752 | A1 | 6/2014 | Sipilä et al. |
| 2014/0175271 | A1 * | 6/2014 | Samson ................ E21B 47/123 250/264 |
| 2014/0191761 | A1 | 7/2014 | San Martin et al. |
| 2014/0208843 | A1 | 7/2014 | Godfrey |

OTHER PUBLICATIONS

Chen et al. "Fiber Optic Magnetic Field Sensor Based on the TbDyFe Rod." Measurement Science and Technology, vol. 25, No. 8, Jul. 14, 2014.

Extended Search Report issued for European Patent Application No. 15887987, dated Oct. 18, 2018, 7 pages.

* cited by examiner

FIBER OPTIC NUCLEAR MAGNETIC RESONANCE SENSOR

PRIORITY

The present application is a U.S. National Stage patent application of International Patent Application No. PCT/US2015/023600, filed on Mar. 31, 2015, the benefit of which is claimed and the disclosure of which is incorporated herein by reference in its entirety.

BACKGROUND

Nuclear magnetic resonance (NMR) logging is a type of well logging that uses the NMR response of a formation to directly determine its porosity and permeability. NMR logging exploits the magnetic moment of hydrogen, which is abundant in rocks in the form of water. The NMR signal amplitude is proportional to the quantity of hydrogen nuclei present in a formation and can be calibrated to give a value for porosity that is free from lithology effects.

NMR logs provide information about the quantities of fluids present in a geological formation, the properties of these fluids, and the sizes of the pores containing these fluids. From this information, it is possible to infer or estimate the volume (porosity) and distribution (permeability) of the rock pore space, the rock composition, the type and quantity of fluid hydrocarbons, as well as the hydrocarbon producibility.

Generally, NMR tools operate by using an imposed magnetic field. This magnetic field is traditionally referred to as the "main magnetic field" or the "static field" as it is usually independent of time and is given the symbol $B_0$. A second magnetic field, which varies in time, is also applied. This field is designated as $B_1$ and is traditionally called the "radio frequency (RF) field". It is turned on and off at different increments, known as a pulse. This perturbing field is usually applied in the form of an RF electromagnetic pulse whose useful magnetic component, $B_1$, is perpendicular to the static field, $B_0$. The perturbing field moves the orientation of the magnetization into the transverse (perpendicular) plane. The frequency of the pulse can be chosen to target specific nuclei (e.g., hydrogen). The polarized nuclei are perturbed simultaneously and, when the perturbation ends, they precess around the static magnetic field gradually re-polarizing to align with the static field while losing coherence in the transverse plane. The precessing nuclei generate a detectable RF signal that can be used to measure statistical distributions that can be converted into measurements of porosity (i.e., the relative amount of void space in the formation), hydrocarbon saturation (i.e., the relative percentage of hydrocarbons and water in the formation fluid), and permeability (i.e., the ability of formation fluid to flow from the formation into the wellbore).

When the $B_1$ magnetic field is created by an RF coil powered by a transmitter, ringing, resonance, and other artifacts of this conventional system may reduce the accuracy and resolution of NMR measurements.

DETAILED DESCRIPTION

Some of the challenges noted above, as well as others, can be addressed by implementing the apparatus, systems, and methods described herein. In many embodiments, a fiber optic sensor is used as a receiving sensor to make electromagnetic measurements. As a result, vertical resolution may be improved producing an improved signal-to-noise ratio. These embodiments will now be described in detail.

Figure 1:
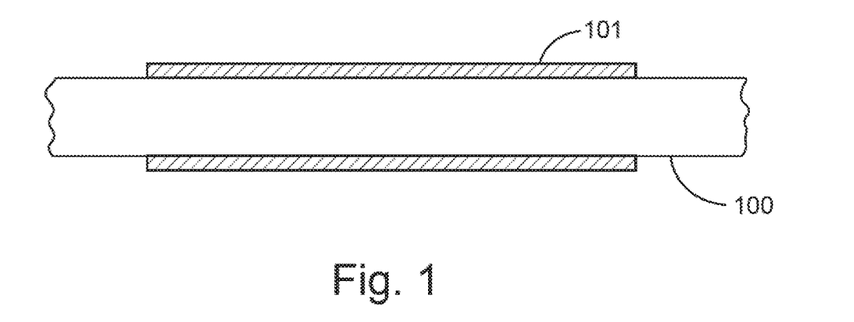
FIG. 1 is a side, cut-away view of a fiber optic sensor element, according to various embodiments of the invention.

FIG. 1 is a side, cut-away view of a fiber optic sensor element, according to various embodiments of the invention. The sensor element comprises an optical fiber 100 that has one or more sections of its length coated with a material 101 that has properties that enable the fiber to phase or amplitude modulate a light signal propagating within the fiber when the material is exposed to a time-varying field (e.g., magnetic, electric). The coating material 101 may include a magnetostrictive material or piezoelectric material, or both.

Magnetostriction is a property of ferromagnetic materials that causes them to change their physical shape or dimensions during the process of magnetization in the presence of a magnetic field. Magnetostrictive materials that may be useful in various embodiments include any material that exhibits a high degree of microstrain in response to a magnetic field (e.g., amorphous alloy). Some materials that exhibit these qualities include cobalt, Terfenol-D (i.e., terbium (Ter), iron (Fe), Naval Ordnance Laboratory (NOL), dysprosium (D), $Tb_xDy_{1-x}Fe_2$), and $Fe_{81}Si_{3.5}B_{13.5}C_2$ (i.e., METGLAS® 2605SC).

A piezoelectric material exhibits a mechanical strain resulting from an applied electrical field. Some piezoelectric materials that may be useful in various embodiments include lead zirconate titanate crystals ($PbTiO_3$), quartz, barium titanate ($BaTiO_3$), potassium niobate ($KNbO_3$), lithium niobate ($LiNbO_3$), zinc oxide (ZnO), lithium tantalate ($LiTaO_3$), and sodium tungstate ($Na_2WO_3$).

When the coated optical fiber is exposed to either a varying magnetic field (for a magnetostrictive material) or a varying electric field (for a piezoelectric material), the resulting microstrain causes a physical perturbation of the optical fiber. This induced microstrain modulates optical phase changes in light waves propagating in the fiber in response to the variations in the field. The field varies over time in frequency and/or amplitude.

Pulsed NMR systems employ a permanent magnet and one or more orthogonal RF induction antennas. The resulting echo signal, after time $T_E$, provides two polarization components that are equal in signal amplitude. A first component is polarized with the transmitting antenna and a second component is orthogonal to both the permanent magnet's static field and the transmitting antenna's RF field. The second component may be received by a fiber optic NMR tool receiver to provide sensitivity to the RF echo's magnetic flux that is correctly polarized for the desired measurement region. Such a device is illustrated in FIG. 2.

Figure 2:
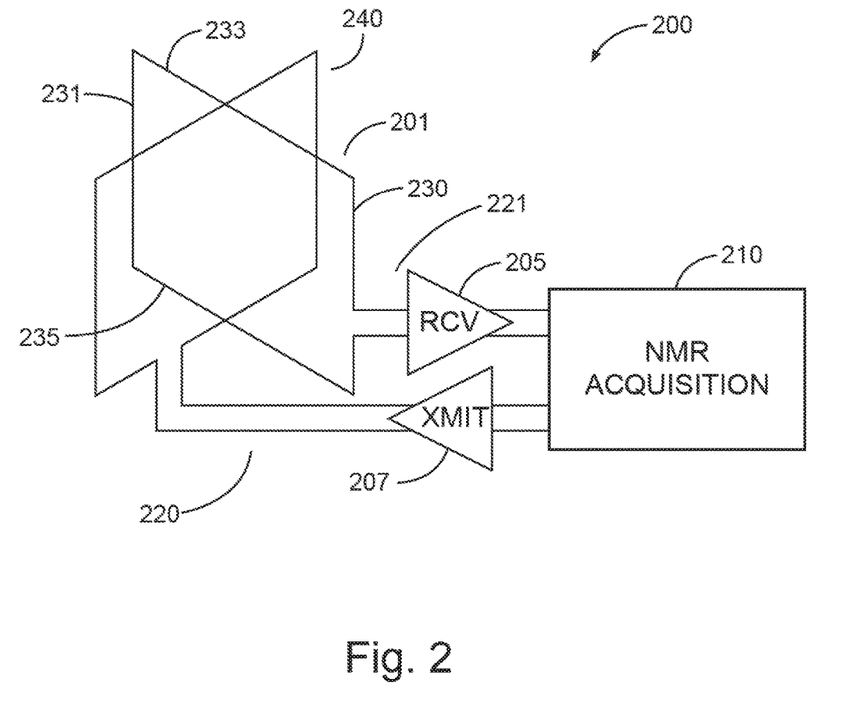
FIG. 2 is a block diagram of a tool including a fiber optic NMR sensor element, according to various embodiments of the invention.

FIG. 2 is a block diagram of a tool including a fiber optic NMR sensor element, according to various embodiments of the invention. Using the coated fiber optic element, the tool may perform NMR measurements in a geological formation in order to determine the characteristics of the formation.

The fiber optic NMR sensor device includes an RF transmit path 220 and a receive path 221 that are coupled to an NMR acquisition block 210 (e.g., NMR acquisition device). The transmit path 220 includes an RF transmitter 207 coupled to an RF transmit antenna structure 240 (i.e., an induction loop antenna, operating as an RF magnetic field radiation apparatus). Thus, the NMR acquisition device 210 is coupled to the transmit antenna structure 240 through the RF transmitter 207.

The receive path 221 includes an optical receiver 205 (e.g., an interferometric receiver) coupled to the NMR acquisition block 210. An optical input of the receiver 205 is coupled to a receive RF sensor 201. The optical receiver 205 converts the light from the receive RF sensor 201 into electrical signals for use by the NMR acquisition block 210. If the received light signals are modulated, as described herein, the receiver 205 outputs modulated electrical signals.

The receive RF sensor 201 includes two fiber optic elements 230, 231 (i.e., sensitive optical fiber) as illustrated previously in FIG. 1. One or both of the fiber optic elements 230, 231 may be coated. The elements 230, 231 are interconnected by non-coated optical fiber 233, 235 (i.e., insensitive optical fiber). The RF sensor 201 is coupled to the receiver 205 through an optical coupling. The sensitive fiber optic sensor elements 230, 231 comprise a magnetically or electrically field sensitive coating.

The NMR acquisition block 210 is configured to generate the signals for conversion to RF by the transmitter 207. The NMR acquisition block 210 is also configured to receive the electrical signals as generated by the receiver 205 and demodulate the electrical signals. As described subsequently, the demodulated signals may include information regarding the characteristics of the geological formation. The NMR acquisition block 210 and/or the transmitter 207 and receiver 205 may be located on or in the tool, or on the surface, such that data resulting from operation of the RF transmit antenna structure 240 and the RF sensor 201 may be communicated via telemetry.

In operation, the NMR acquisition block 210 generates the electrical signals to be transmitted as a magnetic induction field by the RF transmitter 207 through the RF transmit antenna structure 240. The signals may comprises excitation pulses that are relatively large in amplitude (e.g., transmitter may generate approximately 1 kV and approximately 100 Amp, the antenna may radiate approximately 0.2 Volt-Second pulses kilovolts), and transmitted through the borehole into the geological formation to initiate an NMR measurement. Interleaved echo signals from the formation are in the form of magnetic or electric fields that vary in amplitude and/or frequency in response to the formation characteristics. The received signal amplitudes may be many orders of magnitude smaller than the excitation pulse.

The sensitive fiber optic elements 230, 231 are exposed to the varying fields, and the magnetostrictive/piezoelectric material in the elements 230, 231 modulates the light being transmitted through the sensitive and insensitive fiber of the receive RF sensor 201 in response to the field variations. The modulated light signals are converted to modulated electrical signals by the optical receiver 205. The NMR acquisition block 210 may then demodulate the signals to generate the electrical signals that are indicative of the formation properties.

Figure 3:
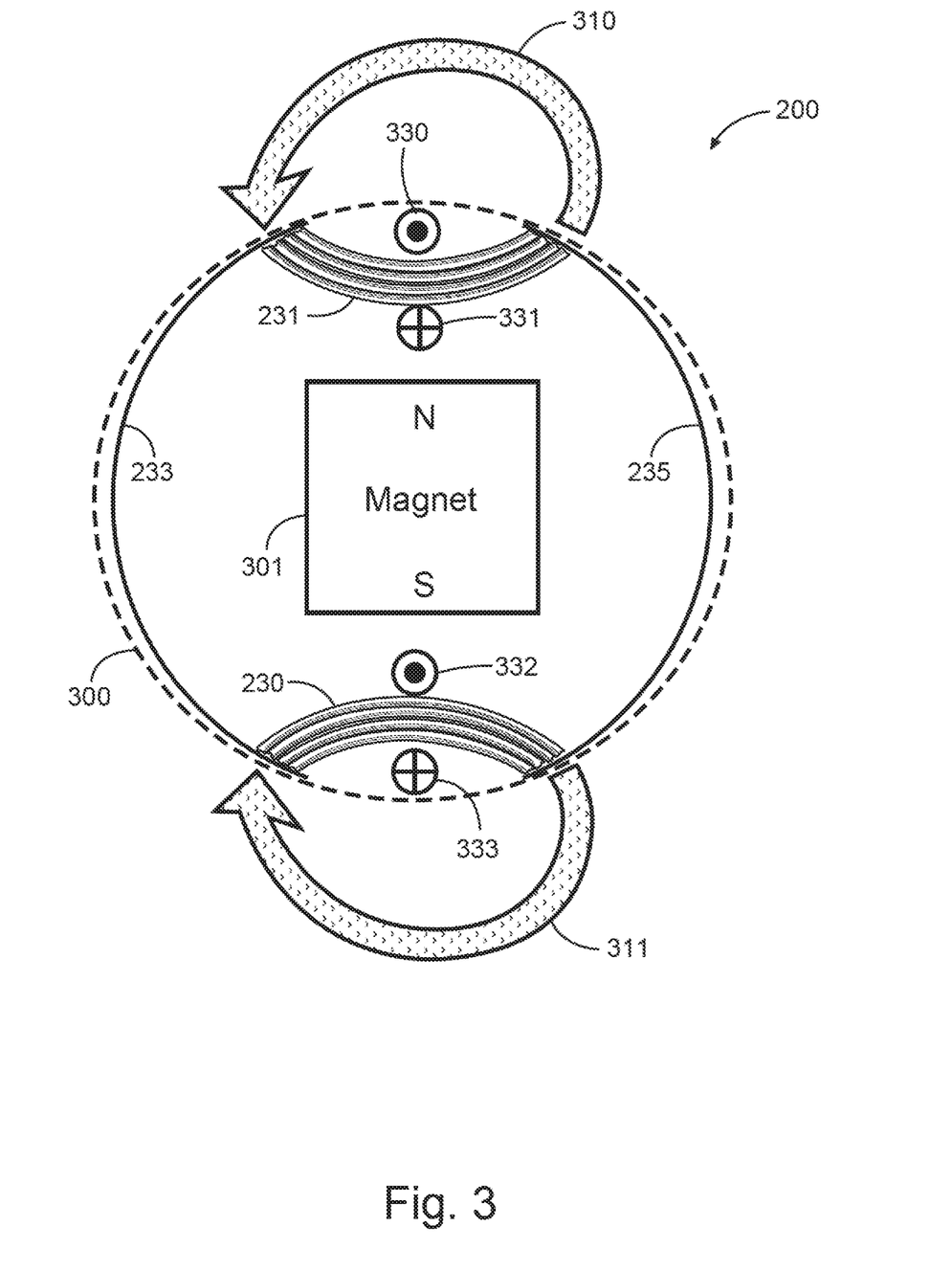
FIG. 3 is a cross-section view of a fiber optic NMR tool receiver configuration, according to various embodiments of the invention.
Figure 5:
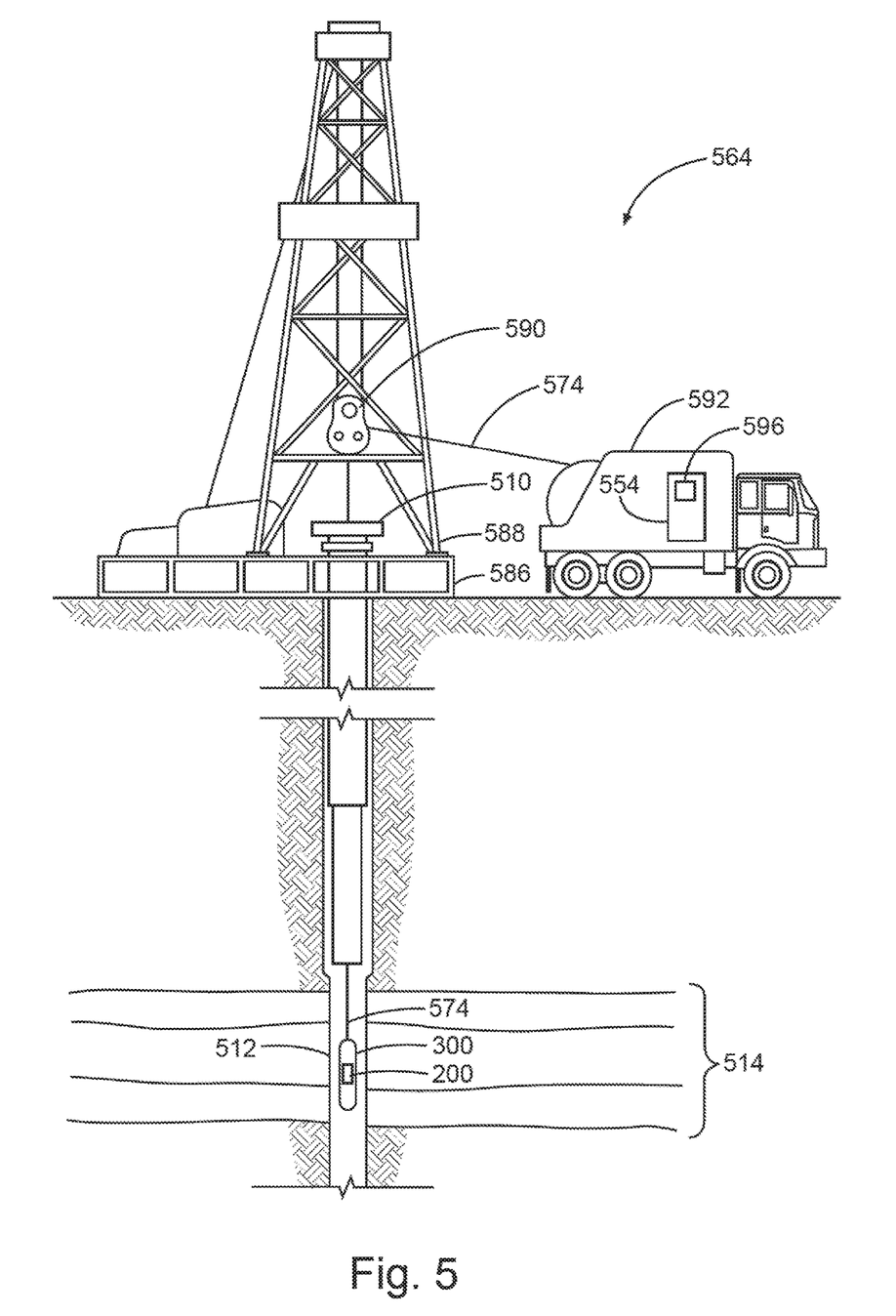
FIG. 5 is a wireline system diagram, according to various embodiments of the invention.
Figure 6:
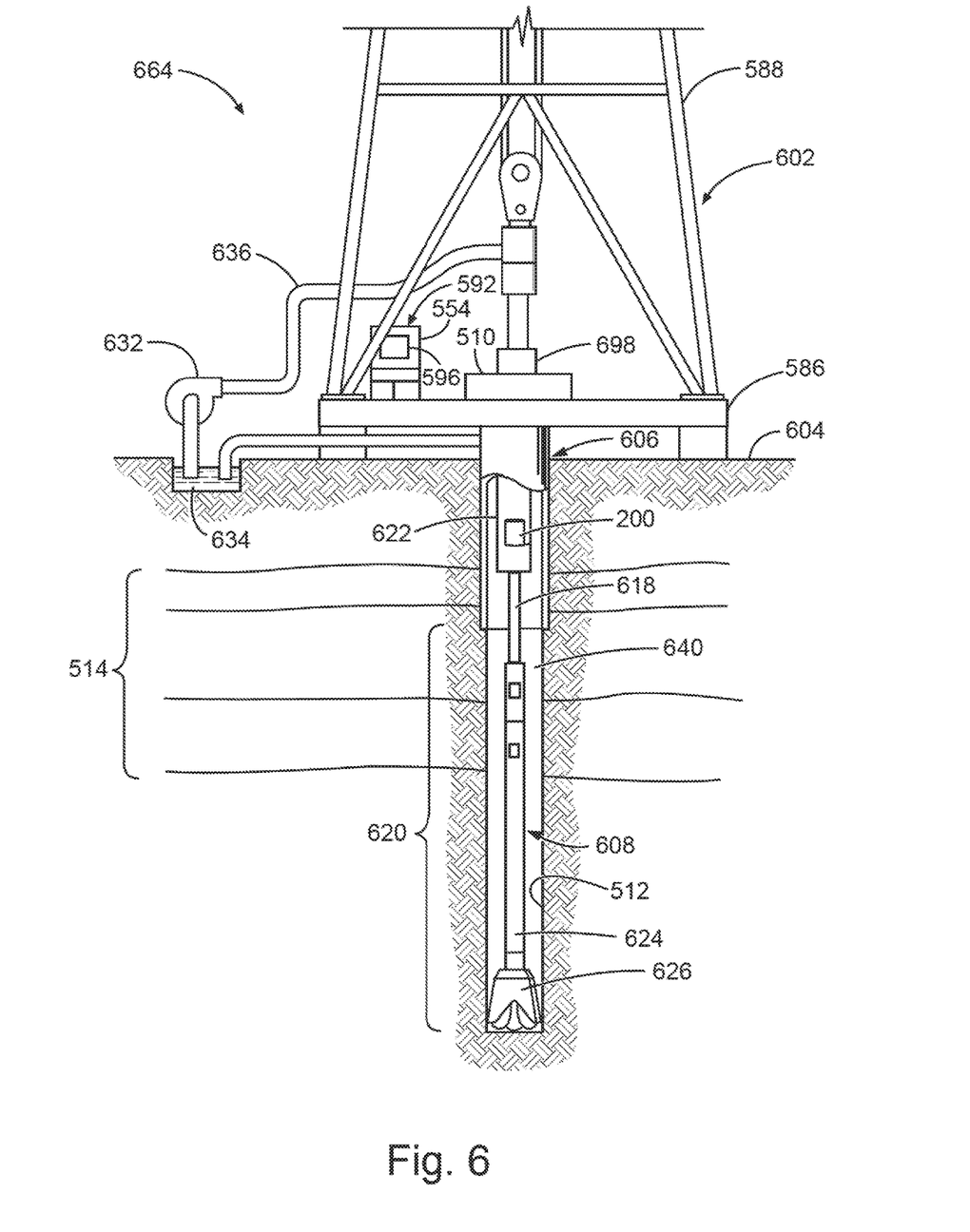
FIG. 6 is a drilling system diagram, according to various embodiments of the invention.

FIG. 3 is a cross-section view of a fiber optic NMR tool receiver configuration, according to various embodiments of the invention. Such a device may be used in a downhole system (e.g., wireline, drilling) as shown in FIGS. 5 and 6 and discussed subsequently.

The tool housing 300 includes the transmit antenna structure elements 330-333 that are part of the RF transmit antenna structure 240 of FIG. 2. The transmit antenna structure 330-333 includes the induction loop antenna that radiates the sensitive measurement volume (not shown) with a magnetic field that has the appropriate magnitude, duration, and directionality for pulsed NMR operation. The transmitter relative current flow is illustrated in FIG. 3 as a dot 330, 332 signifying current flow out of the page and a cross 331, 333 signifying current flow into the page. The RF field 310, 311 generated by the transmitter antenna structure 330-333 is illustrated encircling the antenna to radiate into the geological formation. The RF field 310, 311 is orthogonal to a static magnetic field generated by a magnet 301 (e.g., permanent magnet, electromagnet) in the tool housing 300.

The sensitive fiber optic elements 230, 231 (i.e., coated optical fiber) are formed in the tool housing 300 parallel to the transmitter's magnetic field within the receive RF sensor. One or both of the fiber optic elements may be coated. The magnetostrictive or piezoelectric coating material provides a magnetically/electrically permeable (field sensitive) coating to act as a low reluctance path to the transmitter energy flux, thus enhancing the field strength within the sensitive volume and reducing the transmitter power. Forming the sensitive fiber along the transmitted field lines may also reduce the sensitivity to the transmit pulse and background ringing that can disturb echo reception.

The sensitive fiber optic elements 230, 231 are coupled by the insensitive optical fibers 233, 235. As previously discussed, the insensitive optical fibers 233, 235 are not coated with the magnetostrictive or piezoelectric material but simply provide connectivity to the sensitive fiber optic elements 230, 231. One advantage of the fiber optic sensor element, relative to a conventional induction loop, is that the magnetic field sensitivity is limited to desired regions of the tool 300 and is configured for the selected magnet and transmit antenna configuration. The present embodiments are not limited to only the illustrated antenna/magnet configuration—many others may be realized.

The permanent magnet 301, located substantially proximate to the center of the tool housing 300, provides the static magnetic field that is used for pulsed NMR operations, and is orthogonal to the time-varying magnetic field generated by the transmit antenna. The sensitive fiber is located over the poles (i.e., N and S) of the magnet 301. The permeable coating of the sensitive fiber 230, 231 enhances the magnet's field strength at the sensitive volume, thus improving the signal-to-noise (SNR) ratio. The magnetic bias placed on the coating material is below its saturating flux density and is stabilized by the long magnetic path length beyond the fiber optic structure.

Figure 4:
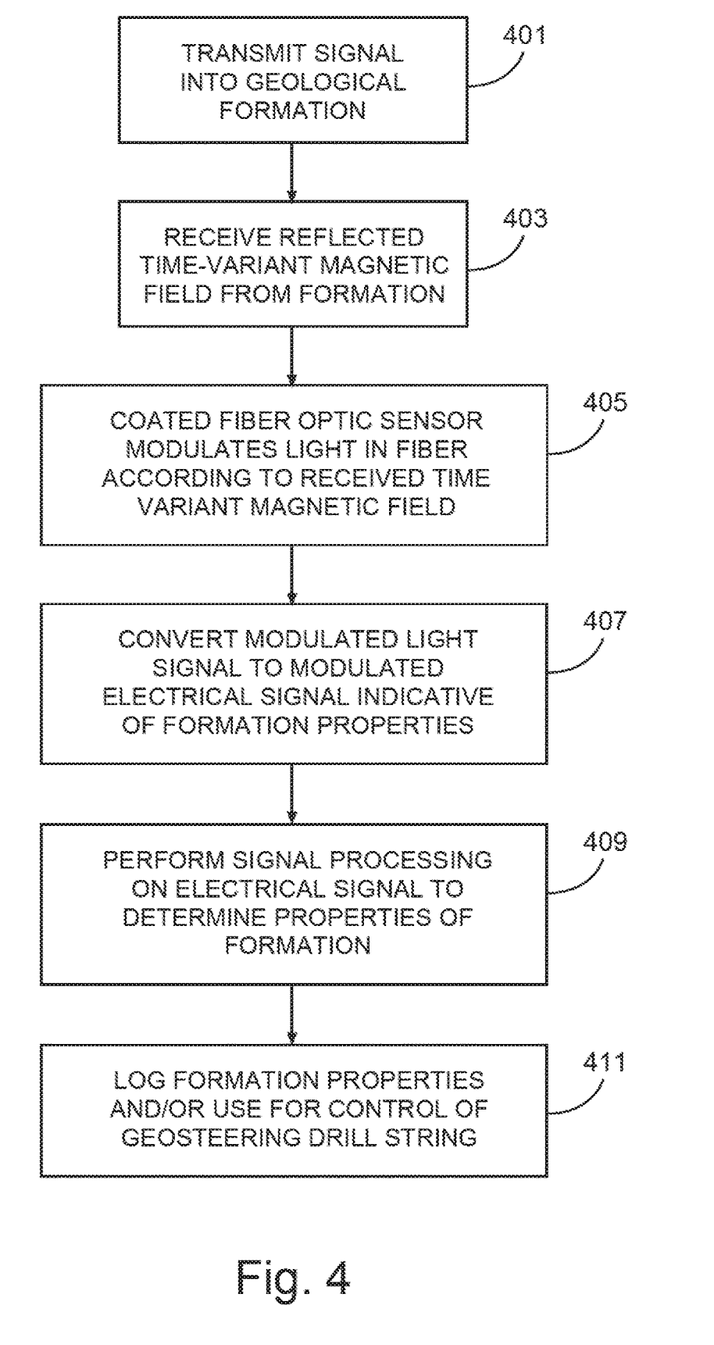
FIG. 4 is a flowchart of a method for making NMR measurements, according to various embodiments of the invention.

FIG. 4 is a flowchart of a method for making NMR measurements, according to various embodiments of the invention. The NMR measurements may be used in a downhole environment to determine geological formation characteristics. For example, wireline and drilling embodiments, as shown in FIGS. 5 and 6 respectively, may use and execute the following method.

Referring now to FIGS. 1-4, it can be seen that in block 401, the method transmits a static magnetic field, from the permanent magnet, and an RF signal into the geological formation. The RF signal is transmitted from the transmit antenna structure 330-333. In block 403, a reflected time variant (e.g., frequency, amplitude) magnetic field is received from the formation after a time $T_E$.

In block 405, the coating on the sensitive fiber optic sensor element modulates the light signal in the fiber according to the received time-variant magnetic field. The modulation of the light signal is representative of the characteristics of the geological formation as indicated by the reflected signal.

In block 407, the modulated light signal from the fiber is converted to a modulated electric signal that is indicative of the formation properties. In block 409, signal processing may be performed on the electrical signal to determine the value of these formation properties. The signal processing may include demodulation of the electrical signal. In block 411; the formation properties may be logged (e.g., wireline or LWD operation) or used for controlling the geosteering of a drill string (e.g., MWD operation).

Using the fiber optic NMR sensor tool may improve vertical resolution in a borehole imaging application, since induction loop sensors use a relatively longer length to provide enough area for collecting sufficient flux to produce a useable SNR. As a matter of contrast, a coated fiber optic element needs only to be exposed to a magnetic field intensity that is above its detectable limit to provide a useful measurement.

Transmitter power may also be reduced relative to typical NMR transmitters. Since the sensitive volume is reduced in size, the transmitting antenna may also be reduced in size, thus reducing exposure to conductive borehole eddy current loss.

Ringing may also be reduced relative to conventional NMR transmit antenna applications. This is because conventional NMR tools typically use one or more receive antennas that resonate in a parallel tank circuit to improve signal strength. Such high Q circuits are sensitive to acoustic ringing in their environments, limiting the receive recover time to acquire an echo signal. As a matter of contrast, a fiber optic NMR sensor uses a non-resonant sensor method that is less prone to ringing, as well as being cross-polarized with the main antenna to further attenuate parasitic ringing sources. Reduced inner echo times (Te) may result from the faster transmit-to-receive recover times.

FIG. 5 is a wireline system diagram, according to various embodiments of the invention. FIG. 6 is a drilling system diagram, according to various embodiments of the invention. The systems 564, 664 may thus comprise portions of a wireline logging tool body 300 as part of a wireline logging operation or of a down hole tool 624. Either of these tools 300, 624 may include the fiber optic NMR sensor tool 200 as described previously.

FIG. 5 illustrates a drilling platform 586 equipped with a derrick 588 that supports a hoist 590. Drilling oil and gas wells is commonly carried out using a string of drill pipes connected together so as to form a drillstring that is lowered through a rotary table 510 into a wellbore or borehole 512. Here it is assumed that the drillstring has been temporarily removed from the borehole 512 to allow a wireline logging tool body 300, such as a probe or sonde with the fiber optic NMR sensor tool, to be lowered by a cable 574 (e.g., wireline or slickline cable) into the borehole 512. Typically, the wireline logging tool body 300 is lowered to the bottom of the region of interest and subsequently pulled upward at a substantially constant speed.

During the upward trip, at a series of depths various instruments may be used to perform NMR measurements on the subsurface geological formations 514 adjacent to the borehole 512 (and the tool body 300). The wireline data may be communicated to a surface logging facility 592 for processing, analysis, and/or storage. In another example, some or all of the processing, analysis, and/or storage may occur in a downhole tool that may be part of the tool body 300 or a separate tool.

The logging facility 592 may be provided with electronic equipment for various types of signal processing. In another embodiment, down-logging may be performed using the wireline logging tool as the tool body 300 is lowered into the borehole 512 and measurements are taken during the downward trip. In some embodiments, the NMR acquisition block 210 of FIG. 2 may be incorporated into the logging facility 592.

In some embodiments, the tool body 300 is suspended in the wellbore by a wireline cable 574 that connects the tool to a surface control unit (e.g., comprising a workstation 554). The tool may be deployed in the borehole 512 on coiled tubing, jointed drill pipe, hard wired drill pipe, or any other suitable deployment technique.

Referring to FIG. 6, it can be seen how a system 664 may also form a portion of a drilling rig 602 located at the surface 604 of a well 606. The drilling rig 602 may provide support for a drillstring 608. The drillstring 608 may operate to penetrate the rotary table 510 for drilling the borehole 512 through the subsurface formations 514. The drillstring 608 may include a drill pipe 618 and a bottom hole assembly 620, perhaps located at the lower portion of the drill pipe 618.

The bottom hole assembly 620 may include drill collars 622, a down hole tool 624 including the fiber optic NMR sensor tool, and a drill bit 626. The drill bit 626 may operate to create the borehole 512 by penetrating the surface 604 and the subsurface formations 514. The downhole tool 624 may comprise any of a number of different types of tools besides the fiber optic NMR sensor including MWD tools, LWD tools, and others. NMR measurements may be performed and the data communicated to a surface logging facility 692 for processing, analysis, and/or storage. In another example, some or all of the processing, analysis, and/or storage may occur in a downhole tool that may be part of the downhole tool 624 or a separate tool.

During drilling operations, the drillstring 608 (perhaps including the drill pipe 618 and the bottom hole assembly 620) may be rotated by the rotary table 510. Although not shown, in addition to, or alternatively, the bottom hole assembly 620 may also be rotated by a motor (e.g., a mud motor) that is located down hole. The drill collars 622 may be used to add weight to the drill bit 626 and to house the fiber optic NMR tool 200 of FIGS. 2 and 3. The tool 200 may be modified to fit into the drill collar and support internal mud flow and mechanical robustness. The downhole tool 624 is configured to geosteer the drill string 608 in response to signals from the fiber optic NMR tool 200 based on the characteristics of the geological formation. The drill collars 622 may also operate to stiffen the bottom hole assembly 620, allowing the bottom hole assembly 620 to transfer the added weight to the drill bit 626, and in turn, to assist the drill bit 626 in penetrating the surface 604 and subsurface formations 514.

During drilling operations, a mud pump 632 may pump drilling fluid (sometimes known by those of ordinary skill in the art as "drilling mud") from a mud pit 634 through a hose 636 into the drill pipe 618 and down to the drill bit 626. The drilling fluid can flow out from the drill bit 626 and be returned to the surface 604 through an annular area 640 between the drill pipe 618 and the sides of the borehole 512.

The drilling fluid may then be returned to the mud pit 634, where such fluid is filtered. In some embodiments, the drilling fluid can be used to cool the drill bit 626, as well as to provide lubrication for the drill bit 626 during drilling operations. Additionally, the drilling fluid may be used to remove subsurface formation cuttings created by operating the drill bit 626.

The workstation 554 and the controller 596 may include modules comprising hardware circuitry, a processor, and/or memory circuits that may store software program modules and objects, and/or firmware, and combinations thereof. The workstation 554 and controller 596 may be configured to control the direction and depth of the drilling in response to formation characteristics as determined by the fiber optic NMR sensor tool.

In either of the systems 564, 664 described previously, data may be communicated to the surface for processing, analysis, and/or storage using some form of telemetry (e.g., wired, wireless, mud pulse). For example, using mud pulse telemetry, the telemetry may be used to modulate the drilling fluid to create a series of momentary pressure changes, or pulses, in the drilling fluid to be detected at the surface workstation 554. Pulse duration, amplitude, and time between pulses, is detected by the workstation 554 and demodulated. Mud pulse telemetry may include various methods for introducing positive or negative pressure pulses into the drilling fluid. The above-described apparatuses, methods, and/or systems are further described in the following examples:

Example 1 is a nuclear magnetic resonance (NMR) sensor device, comprising a magnet that generates a static magnetic field; a transmit antenna to transmit a time-varying magnetic field at selected locations within a formation; and a sensitive fiber optic sensor element having a coating to modulate a light signal in the sensor element in response to being exposed to a received time-varying magnetic field resulting from the transmitted time-varying magnetic field.

In Example 2, the subject matter of Example 1 can further include wherein the time-varying magnetic field is orthogonal to the static magnetic field.

In Example 3, the subject matter of Examples 1-2 can further include an interferometric receiver coupled to the sensitive fiber optic sensor element.

In Example 4, the subject matter of Examples 1-3 can further include wherein the interferometric receiver is coupled to the sensitive fiber optic sensor element through insensitive optical fiber.

In Example 5, the subject matter of Examples 1-4 can further include wherein the sensitive fiber optic sensor element is located in the device and disposed parallel to the time-varying magnetic field.

In Example 6, the subject matter of Examples 1-5 can further include wherein the sensitive fiber optic sensor element is located substantially adjacent a pole of the magnet.

In Example 7, the subject matter of Examples 1-6 can further include wherein the coating comprises one of a magnetostrictive material or a piezoelectric material to phase modulate the light signal in the sensitive fiber optic sensor element.

In Example 8, the subject matter of Examples 1-7 can further include wherein the sensitive fiber optic sensor element comprises a plurality of sections of coated optical fiber coupled together by sections of uncoated optical fiber.

In Example 9, the subject matter of Examples 1-8 can further include wherein the coating is divided into sections, and wherein some of the sections are located at different poles of the magnet.

Example 10 is a nuclear magnetic resonance (NMR) sensor device, comprising a permanent magnet that generates a static magnetic field; a transmit antenna structure to transmit a time-varying magnetic field in a sensitive volume, the transmit antenna structure comprising an RF magnetic field radiation apparatus; a receive sensor comprising a sensitive fiber optic sensor element having a coating to phase modulate or amplitude modulate a light signal in the element in response to amplitude or frequency variations in an echo signal resulting from the time-varying magnetic field; and an optical receiver coupled to the receive sensor, the optical receiver configured to provide a modulated electrical signal representative of the phase modulated light signal.

In Example 11, the subject matter of Example 10 can further include an NMR acquisition device coupled to the transmit antenna structure through a radio frequency transmitter.

In Example 12, the subject matter of Examples 10-11 can further include wherein the NMR acquisition device is coupled to the optical receiver and configured to demodulate the electrical signal.

In Example 13, the subject matter of Examples 10-12 can further include wherein the sensitive fiber optic sensor element comprises a magnetically or electrically field sensitive coating.

Example 14, is a borehole inspection system, comprising: a downhole tool housing including a fiber optic nuclear magnetic resonance (NMR) sensor tool, the sensor tool comprising a magnet that generates a static magnetic field; a transmit antenna configured to transmit a time-varying magnetic field that is orthogonal to the static magnetic field; and a sensitive fiber optic sensor element having a coating configured to phase or amplitude modulate a light signal in the element in response to amplitude and/or frequency variations in a reflected signal resulting from the time-varying magnetic field.

In Example 15, the subject matter of Example 14 can further include wherein the system comprises a wireline tool and the downhole tool is disposed in the wireline tool.

In Example 16, the subject matter of Examples 14-15 can further include wherein the fiber optic NMR sensor is coupled to a logging system for logging geological formation characteristics.

In Example 17, the subject matter of Examples 14-16 can further include wherein the system comprises a drill string tool and the downhole tool is disposed in the drill string tool.

In Example 18, the subject matter of Examples 14-17 can further include wherein the downhole tool is configured to geosteer the drill string in response to signals from the fiber optic NMR sensor.

Example 19 is a method for making nuclear magnetic resonance (NMR) measurements, the method comprising transmitting a time-variant radio-frequency signal into a geological formation; receiving a reflected time-variant signal from the geological formation; and modulating light in a fiber optic sensor element exposed to the reflected time-variant signal, in response to the reflected time-variant signal, the modulated light signal indicative of characteristics of the geological formation.

In Example 20, the subject matter of Example 19 can further include wherein the time-variant RF signal varies over time in amplitude or frequency.

In Example 21, the subject matter of Examples 19-20 can further include converting the modulated light signal to a modulated electrical signal; and demodulating the electrical signal to determine the characteristics of the geological formation.

In Example 22, the subject matter of Examples 19-21 can further include logging the characteristics of the geological formation.

In Example 23, the subject matter of Examples 19-22 can further include geosteering a drill string in response to the characteristics of the geological formation.

This detailed description refers to the accompanying drawings that show, by way of illustration and not limitation, various embodiments in which the invention may be practiced. These embodiments are described in sufficient detail to enable those of ordinary skill in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. This detailed description is, therefore, not to be taken in a limiting sense.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Although specific embodiments have been illustrated and described herein, it should be appreciated that any arrangement configured to achieve the same purpose may be substituted for the specific embodiments shown. This disclosure is intended to cover any and all adaptations or variations of various embodiments. Combinations of the above embodiments, and other embodiments not described herein, will be apparent to those of skill in the art upon reviewing the above description.

What is claimed is:

1. A nuclear magnetic resonance (NMR) sensor device, comprising:
    a magnet that generates a static magnetic field, the magnet having a north pole and opposing south pole;
    a transmit antenna to transmit a time-varying magnetic field at selected locations within a formation; and
    a sensitive fiber optic sensor element having a coating to modulate a light signal in the sensor element in response to being exposed to a received time-varying magnetic field resulting from the transmitted time-varying magnetic field, the sensitive fiber optic sensor element comprising a first and second sensor element,
    wherein the first sensor element is located adjacent the north pole of the magnet and the second sensor element is located adjacent the south pole of the magnet.

2. The sensor device of claim 1, wherein the time-varying magnetic field is orthogonal to the static magnetic field.

3. The sensor device of claim 1, further comprising an interferometric receiver coupled to the sensitive fiber optic sensor element.

4. The sensor device of claim 3, wherein the interferometric receiver is coupled to the sensitive fiber optic sensor element through insensitive optical fiber.

5. The sensor device of claim 1, wherein the sensitive fiber optic sensor element is located in the device and disposed parallel to the time-varying magnetic field.

6. The sensor device of claim 1, wherein the coating comprises one of a magnetostrictive material or a piezoelectric material to phase modulate the light signal in the sensitive fiber optic sensor element.

7. The sensor device of claim 1, wherein the sensitive fiber optic sensor element comprises a plurality of sections of coated optical fiber coupled together by sections of uncoated optical fiber.

8. The sensor device of claim 1, wherein the coating is divided into sections, and wherein some of the sections are located at different poles of the magnet.

9. A nuclear magnetic resonance (NMR) sensor device, comprising:
    a permanent magnet that generates a static magnetic field, the magnet having a north pole and opposing south pole;
    a transmit antenna structure to transmit a time-varying magnetic field in a sensitive volume, the transmit antenna structure comprising an RF magnetic field radiation apparatus;
    a receive sensor comprising a sensitive fiber optic sensor element having a coating to phase modulate or amplitude modulate a light signal in the element in response to amplitude or frequency variations in an echo signal resulting from the time-varying magnetic field, the sensitive fiber optic sensor element having a first sensor element and a second sensor element;
    wherein the first sensor element is located adjacent the north pole of the magnet and the second sensor element is located adjacent the south pole of the magnet, and
    an optical receiver coupled to the receive sensor, the optical receiver configured to provide a modulated electrical signal representative of the phase modulated light signal.

10. The sensor device of claim 9, further comprising an NMR acquisition device coupled to the transmit antenna structure through a radio frequency transmitter.

11. The sensor device of claim 10, wherein the NMR acquisition device is coupled to the optical receiver and configured to demodulate the electrical signal.

12. The sensor device of claim 9, wherein the sensitive fiber optic sensor element comprises a magnetically or electrically field sensitive coating.

13. A borehole inspection system, comprising:
    a downhole tool housing including a fiber optic nuclear magnetic resonance (NMR) sensor tool, the sensor tool comprising:
        a magnet that generates a static magnetic field, the magnet having a north pole and opposing south pole;
        a transmit antenna configured to transmit a time-varying magnetic field that is orthogonal to the static magnetic field; and
        a sensitive fiber optic sensor element having a coating configured to phase or amplitude modulate a light signal in the element in response to amplitude and/or frequency variations in a reflected signal resulting from the time-varying magnetic field, the sensitive fiber optic sensor element having a first sensor element and a second sensor element, wherein the first sensor element is located adjacent the north pole of the magnet and the second sensor element is located adjacent the south pole of the magnet.

14. The borehole system of claim 13, wherein the system comprises a wireline tool and the downhole tool is disposed in the wireline tool.

15. The borehole system of claim 14, wherein the fiber optic NMR sensor is coupled to a logging system for logging geological formation characteristics.

16. The borehole system of claim 13, wherein the system comprises a drill string tool and the downhole tool is disposed in the drill string tool.

17. The borehole system of claim 16, wherein the downhole tool is configured to geosteer the drill string in response to signals from the fiber optic NMR sensor.

18. A method for making nuclear magnetic resonance (NMR) measurements, the method comprising:
   generating a static magnetic field using a magnet having a north pole and opposing south pole;
   transmitting a time-variant radio-frequency signal into a geological formation;
   receiving a reflected time-variant signal from the geological formation; and
   modulating light in a fiber optic sensor element exposed to the reflected time-variant signal, in response to the reflected time-variant signal, the modulated light signal indicative of characteristics of the geological formation,
   wherein the fiber optic sensor element has a first sensor element and a second sensor element, the first sensor element is located adjacent the north pole of the magnet and the second sensor element is located adjacent the south pole of the magnet.

19. The method of claim 18, wherein the time-variant RF signal varies over time in amplitude or frequency.

20. The method of claim 18, further comprising:
   converting the modulated light signal to a modulated electrical signal; and
   demodulating the electrical signal to determine the characteristics of the geological formation.

21. The method of claim 20, further comprising logging the characteristics of the geological formation.

22. The method of claim 20, further comprising geosteering a drill string in response to the characteristics of the geological formation.

* * * * *